(12) United States Patent
Xie et al.

(10) Patent No.: US 6,844,486 B1
(45) Date of Patent: Jan. 18, 2005

(54) NAC1—A PLANT GENE ENCODING A TRANSCRIPTION FACTOR INVOLVED IN COTYLEDON AND LATERAL ROOT DEVELOPMENT

(75) Inventors: Qi Xie, Singapore (SG); Nam-Hai Chua, New York, NY (US)

(73) Assignee: Temasek Life Sciences Laboratory, Singapore (SG)

( * ) Notice: Subject to any disclaimer, the term of this patent is extended or adjusted under 35 U.S.C. 154(b) by 0 days.

(21) Appl. No.: 09/889,926

(22) PCT Filed: Feb. 11, 1999

(86) PCT No.: PCT/SG99/00011

§ 371 (c)(1),
(2), (4) Date: Sep. 18, 2001

(87) PCT Pub. No.: WO00/47742

PCT Pub. Date: Aug. 17, 2000

(51) Int. Cl.[7] ......................... C12N 15/29; C12N 15/87; A01H 5/00
(52) U.S. Cl. ........................ 800/290; 800/278; 800/298; 536/23.6; 435/468; 435/419
(58) Field of Search ................................. 800/290, 278, 800/298, 287; 536/23.6, 23.1; 435/468, 419

(56) References Cited

FOREIGN PATENT DOCUMENTS

WO     WO 98/56811 A2    12/1998

OTHER PUBLICATIONS

Bowie et al (1990, Science 247:1306–10).*
McConnell et al (2001, Nature 411 (6838):709–713).*
Takada et al. (2001, Development 128:1127–1135).*
Brockmann et al. (2001, Plant and Cell Physiology 42(9):942–951).*
Aoyama et al (1997, The Plant Journal 11:605–612).*
Shinn et al., "Genomic sequence for Arabidopsis thaliana BAC F14J16; AC AC002304," EMBL Database, Jun. 24, 1997.
Xia et al., "Identification of plant cytoskeletal, cell cycle–related and polarity–related proteins using *Schizosaccharomyces pombe*," Plant Journal 10(4):761–769, 1996.
Aida et al., "Genes Involved in Organ Separation in Arabidopsis: An Analysis of the *cup–shaped cotyledon* Mutant," The Plant Cell 9:841–857, Jun. 1997.
Souer et al., "The No Apical Meristem Gene of Petunia Is Required for Pattern Formation in Embryos and Flowers and Is Expressed at Meristem and Primordia Boundaries," Cell 85:159–170, Apr. 19, 1996.

* cited by examiner

Primary Examiner—Phuong T. Bui
Assistant Examiner—Stuart F. Baum
(74) Attorney, Agent, or Firm—Rothwell, Figg, Ernst & Manbeck

(57) ABSTRACT

A novel gene, nacl, has been isolated from Arabidopsis. This gene encodes a protein (NACl) which has been identified as a member of the NAC family. NACl shares a high amino acid sequence homology with other members of the NAC gene products in the N-terminus. Data show that NACl belongs to a newly identified family of transcription factors. NACl is involved in the regulation of cotyledon and lateral root development. Overexpression of the gene can lead to larger plants with larger roots and more lateral roots than in wild-type plants.

8 Claims, 8 Drawing Sheets

A

B

C

| pGB | pGA | interaction |
|---|---|---|
| 1-324 | 1-324 | + |
| 1-199 | 1-324 | + |
| 1-199 | 1-199 | + |
| 1-199 | 1-142 | - |
| 1-199 | 143-324 | - |

-Dex
+Dex

WT

OvereXpress

-Dex   +Dex

WT

Antisense

NAC1— A PLANT GENE ENCODING A TRANSCRIPTION FACTOR INVOLVED IN COTYLEDON AND LATERAL ROOT DEVELOPMENT

BACKGROUND OF THE INVENTION

The NAC genes (including NAM, ATAF1, ATAF2 and CUC2) belong to a relatively large gene family found only in plants thus far. These genes encode proteins which are conserved in their N-terminal ~170 amino acids but are highly divergent in their C-termini. Previous genetic studies in petunia (Souer et al., 1996) and Arabidopsis (Aida et al., 1997) have suggested that some members of the NAC family play a role in patterning of the shoot and floral meristem.

Petunia embryos carrying the no apical meristem (nam) mutation fail to develop a shoot apical meristem. Occasional shoots on nam seedlings bear flowers that develop ten instead of five primordia in the second whorl. Double mutants with the homeotic gene green petals show that nam acts independently of organ identity in whorl 2 and also affects primordium number in whorl 3. Strikingly, nam mRNA accumulates in cells at the boundaries of meristems and primordia. It has been shown that nam plays a role in determining positions of meristems and primordia (Souer et al., 1996).

Mutations in CUC1 and CUC2 (for CUP-SHAPED COTYLEDON), which are genes of Arabidopsis, cause defects in the separation of cotyledons (embryonic organs), sepals, and stamens (floral organs) as well as in the formation of shoot apical meristems. These defects are most apparent in the double mutant. Phenotypes of the mutants suggest a common mechanism for separating adjacent organs within the same whorl in both embryos and flowers. The CUC2 gene was cloned and found to encode a protein homologous to the petunia NAM protein (Aida et al., 1997).

The publications and other materials used herein to illuminate the background of the invention or provide additional details respecting the practice, are incorporated by reference, and for convenience are respectively grouped in the appended List of References.

SUMMARY OF THE INVENTION

A new Arabidopsis NAC family member, NAC1l, is described. This gene was originally isolated by the ability of its cDNAs to alter yeast *S. pombe* cell morphology when overexpressed by using the method of Xia et al. (1996). Northern analysis showed that NAC1 was expressed in a tissue-specific manner with high levels in root and low levels in leaves. Whole-mount in situ experiments showed expression in actively dividing root and shoot meristems.

NAC1 shares a high amino acid sequence homology with other members of the NAC1 gene products in the N-terminus. In vitro DNA binding studies utilizing a recombinant GST-NAC protein and different truncated NAC1 derivatives demonstrated an interaction between the −90 region of the 35S promoter and the conserved N-terminal domain of the protein. Interestingly, yeast assays show that the C-terminus of NAC1 fused to a GAL4 DNA-binding domain can activate transcription. Analysis of different deletion fusions showed that the transactivation domain is located in the C-terminus of the NACl protein. In addition, two-hybrid assays demonstrated that NACl can homodimerize and that the dimerization domain is located in the conserved N-terminal region of the protein. A 21 bp putative bipartite nuclear localization signal sequence was found in the N-terminal conserved NAC domain. Transgenic Arabidopsis were generated using a GFP-NAC1 fusion construct under the control of a dexamethasone (Dex) inducible promoter-GVG system. Analysis of transgenic lines expressing a GFP-NACl fusion protein under Dex induction condition revealed nuclear localization of the chimeric polypeptide in vivo. These data indicate that NAC1 belongs to a newly identified family of transcription factors.

One aspect of the invention is a transgenic plant comprising a gene which encodes NAC1 or a functionally equivalent protein (meaning a protein which binds to the same DNA binding site as does NAC1 and which is at least 70% identical with, preferably 80% identical with, more preferably 90% identical with, and most preferably at least 95% identical with NAC1) which causes the transgenic plant to grow larger than a nontransgenic plant. The plant may be larger because it is heavier, because it has bigger leaves, because it has thicker stems, because it has more roots, and/or because it has larger roots.

A second aspect of the invention is a gene encoding NAC1 or a functionally equivalent protein wherein plants which are transgenic for this gene grow larger than a nontransgenic plant.

A third aspect of the invention is NACl or a functionally equivalent protein wherein if a plant is made transgenic for a gene encoding NAC1 or said functionally equivalent protein said transgenic plant will grow larger than a plant which is not transgenic.

Another aspect of the invention is a transgenic plant cell which contains a gene encoding NAC1 or a functionally equivalent protein which causes the plant cell to grow larger than a nontransgenic cell.

DETAILED DESCRIPTION OF THE INVENTION

Figure 1:
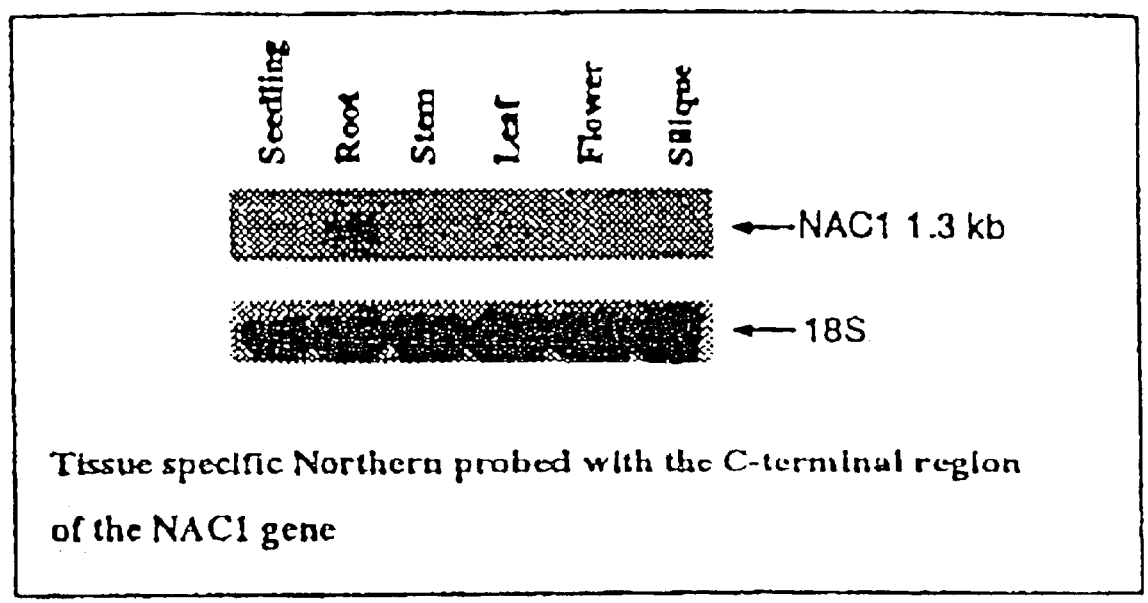
FIG. 1. Tissue specific expression of NACl gene. Autoradiography of RNA gel blots containing 10 ig of total RNAs isolated from different tissues, as labeled. Seedlings were harvested from two weeks old plants. Cauline leaves (leaf), main and lateral stems (stem), flower clusters (flower), and siliques of different stages were harvested from 35 to 40 days old soil growth plants. Roots were taken from two weeks vertical growth seedlings on SM plate. The filter was hybridized with radiolabeled C-terminal of NAC1 and then reprobed with the radiolabeled 18S rDNA probe as a loading control.

The nac1 gene was isolated in a project to isolate plant cytoskeletal, cell cycle-related and polarity-related proteins using *Schizosaccharomyces pombe*. An *A. thaliana* cDNA library under the control of the thiamine-repressible nmt1 promoter of pREP5N was transformed into wild type *S. pombe* cells. One transformant showed elongated cells and multiseptimas when the promoter was depressed. A cDNA clone was isolated from this transformant and retransformed into *S. pombe* to confirm the cell shape change is due to expression of the cDNA. The isolated cDNA (At012) encodes a single open reading frame (ORF) of 324 amino acids (SEQ ID NO:2). The putative protein sequence was searched against GenBank. A BLAST search indicated that the protein is novel. The N-terminus of the protein was found to contain a NAC domain, a domain found in members of the NAC gene family (NAM, ATAF1, ATAF2, CUC2). This domain covers the first 175 amino acids of the protein. The rest of the protein encoded by nacl has no high homology to any known sequence.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

The NAC family of genes has been identified only in plants. These genes encode proteins which are highly conserved in the N-terminus but which vary in the rest of the protein. The first two members, ATAF1 and ATAF2, were from Arabidopsis and were isolated by their ability to activate the 35S cauliflower mosaic virus (CaMV) promoter in yeast (H. Hirt, GenBank Accession Numbers X74755 and X74756). SENU5 cDNA, isolated in studies of leaf senescence in tomato (GenBank Accession Number Z75524; John et al., 1997), and the NAM protein (Souer et al., 1996), the product of the petunia nam gene, are required for proper development of shoot apical meristems and have been proposed to determine meristem location. CUC2 (Aida et al., 1997) is a member of the NAM family and is an Arabidopsis homologue of NAM. The Arabidopsis NAP protein is also a member of the family (Sablowski and Meyerowitz, 1998). Finally, GRAB1 (GenBank Accession Number AJ010829) and GRAB2 (GenBank Accession Number AJ010830) are two more recently reported members of the NAC family. These are from wheat and can interact with wheat dwarf virus (WDV) RepA protein. The trans-overexpression of GRAB1 and GRAB2 genes under the control of 35S promoter can inhibit the WDV replication in wheat cell culture.

The work reported here details the NAC domain in five blocks based on the conservation and the charge of each block. Sequence alignment of NAC1 protein with all these proteins revealed that NAC1 has similar features with other NAC family members which corresponds to the recently identified NAC domain.

The genomic structure of nac1 was analyzed by comparing the genomic sequence with the cDNA sequence. The NACl gene is located on chromosome 1. It includes two introns in the N-terminal coding region. The first intron is 1215 base pairs and occurs within the codon for amino acid 67. The second intron is 102 base pairs and is located between codons for amino acids 160 and 161. A domain search was performed and led to the identification of a putative bipartite nuclear localization signal within the NAC domain of NAC1. This 21 amino acid signal sequence is located from amino acid, 117 to 137 and was the first found in a member of the NAC family. Performing the same search with the other reported NAC family members failed to reveal a similar signal. NAC homologues were seen in a rice EST database but no homologues were seen in other organisms such as mammalian, Drosophila and yeast.

Developmental Regulation of the NAC1 Gene

To investigate the roles of the NAC1 gene during plant development, its expression pattern was analyzed by Northern analysis using a nac1 specific probe. Because members of the NAC family are very conserved at the N-termini even at the DNA level, a C-terminal probe was used. 10 ig of total RNA from each tissue was used for hybridization. A relatively high level of expression of nac1 RNA was detected in the roots (FIG. 1). A lower expression was seen in two week old seedlings which contain all vegetative tissue. Very low expression was detected in material obtained from stems and leaves. No expression was detected in the mixed stages of siliques and mixed mature flower and inflorescence, even after a long exposure.

Figure 2:
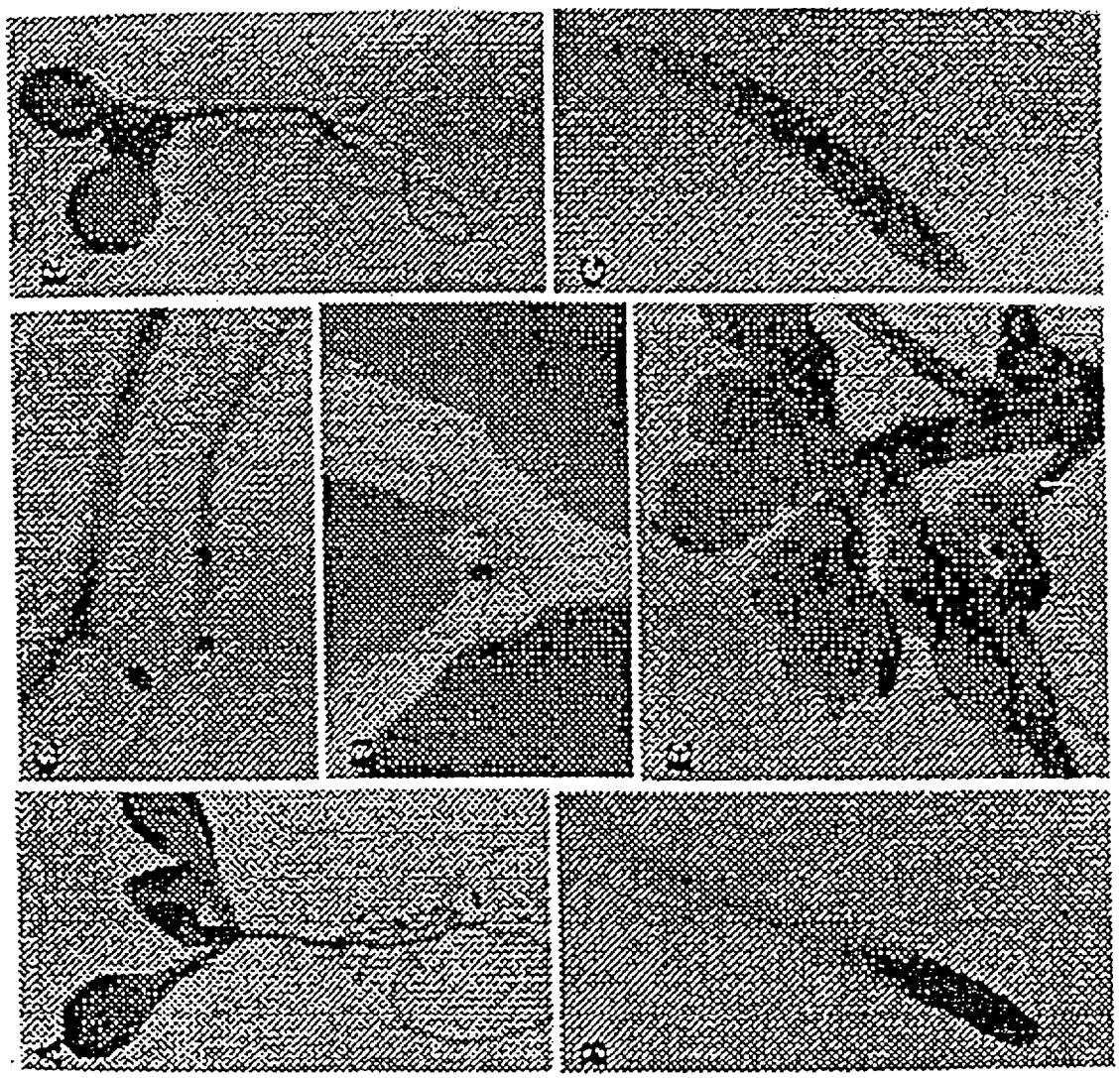
FIG. 2. Whole mount in silu study of NACl in seedlings and flowers. Whole-mount in situ hybridization were performed in seedling and flower with a digoxigenin-labeled (DIG) C-terminal specific antisense probe (A, B, C, D and E) and with a DIG labeled sense probe (F and G). A and F are 12 days old seedlings. Root materials are form 12 day seedling and D is 7 day old seedling. Flowers were taken from 40 day old soil growth plants.

Whole-mount in situ studies of 7 day and 12 day plants were performed using both sense and antisense probes to C-terminal encoding region of the gene. nac1 expression was seen in actively dividing roots and shoot apical meristems (FIG. 2). Expression was especially high in the root tip dividing region (FIGS. 2A and 2B) and lateral root formation region (FIG. 2C). A lower expression was detected in cotyledon and young leaf. These results all correspond to the Northern results. No clear specific hybridization was detected in flower (FIG. 2E). Also, no signal was detected in siliques and stems (data not shown). No specific signal was observed in seedlings hybridized with sense RNA probe (FIGS. 2F and 2G).

DNA Binding and DNA Binding Domains

The first two NAC family genes, ATAF1 and ATAF2, were cloned by their ability to activate a cauliflower mosaic virus (CaMV) 35 S promoter construct in yeast. These two proteins, as well as the other NAC family genes, are conserved in N-terminal NAC domain. The GRAB1 and GRAB2 proteins from wheat also bind to the 35S promoter −500 region. The CaMV 35S promoter contains several known DNA binding elements. A number of plant transcriptional factors have been identified as binding to different elements in the regulatory region of the promoter.

Figure 3:
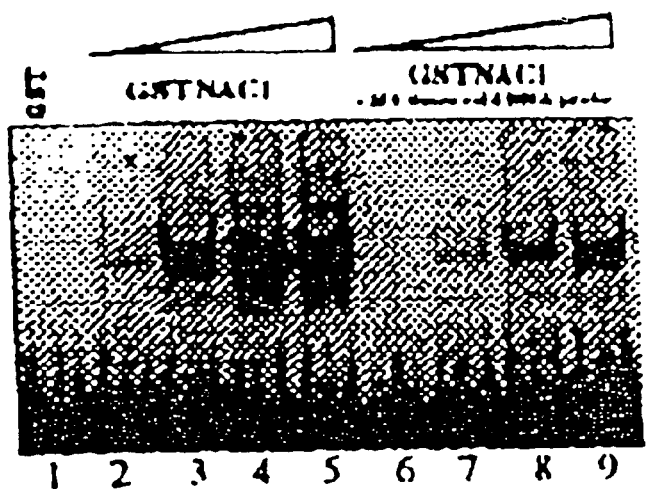
FIG. 3. GST-NAC1 fusion protein binding to CaMV 35S promoter −90 region. (A) Affinity of GST-NAC1 fusion protein binding to 35S promoter −90 regions. Amount of proteins is as follows: Lane 1, 500 ng GST protein. Lanes 2 to 9 are NAC1 fusion proteins. Lanes 2 and 6, 10 ng; lanes 3 and 7, 100 ng; lanes 4 and 8, 250 ng; lanes 5 and 9, 500 ng. As the cold competitor, unlabeled same fragment of DNA was used. (B) Map of different deletions of NAC1 fusion to GST. (C) Different deletions of NACl fusion protein binding to −90 region of CaMV 35S promoter. 20 ng of each recombined protein was used.
Figure 3:
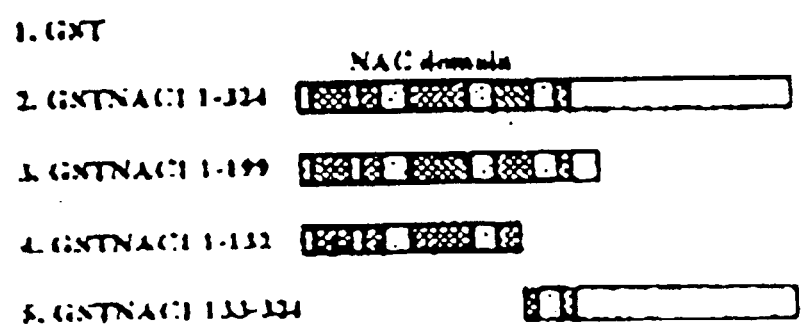
Figure 3:
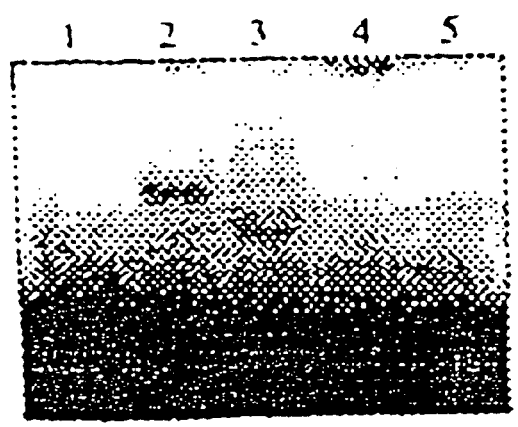

To test whether NAC1 protein could bind to the 35S promoter, the −90 region of the 35S promoter was first used as a probe. nac1 was cloned into the GST fusion vector pGEX-4-2T and transformed into E. coli. The recombinant GST fusion protein was purified and an assay was performed to test for specific binding to DNA. Since a GST fusion protein was being assayed, GST itself was used as a control. GST had no ability to bind to the −90 region of the 35S promoter even when 500 ng of purified protein was used (see FIG. 3A). Different amounts of purified GSTNAC1 protein were tested. Binding was detected with as little as 10 ng of protein and with only 4 hours of exposure of the film (FIG. 3A). It must be noted that the purified GST protein contained only about 10% of intact GST fusion form. Most of the protein degraded during the bacterial growth and purification. This is because after IPTG is added to induce the protein expression, the bacteria can not grow well and the protein begins to degrade before the purification. The addition of excess cold 35S promoter competitor DNA abolished the formation of DNA-protein complex in a concentration-dependent manner (FIG. 3A). These results demonstrate that NAC1 protein binds specifically to the −90 region of the 35S promoter.

Binding of NAC1 to an AS-1 element and a mutant form of the element, −83 to −63 of the 35S promoter, was also tested. Plant zip transcription factors have been identified as binding to this region. The binding affinity was reduced and no clear difference was found between the original AS-1 element and the mutated form. This result indicates that NAC1 had a different DNA binding site than bZIP transcriptional factors and the sequences around the AS-1 element are important for specific binding of NAC1.

To test the DNA binding domain of NAC1, different deletion forms of nac1 were cloned in the GST fusion vector and the fusion proteins were isolated to test the DNA binding ability to the −90 region of the 35S promoter. 20 ng of each protein was used in this assay. The results are shown in FIG. 3C. The truncated form GSTNAC1 contained the first 199 amino acids, the intact NAC domain. This maintained similar binding specific to the DNA probe. A truncated version containing only the first 3 intact blocks of the NAC domain and part of block IV lost the DNA binding ability. Similarly, the complementation of this deletion form, the rest of the protein containing part of block IV and intact block V does not bind to the DNA probe. Together these results indicate that the DNA binding domain is located in the NAC domain and that block IV is important for DNA binding and block V is not enough for DNA binding.

NAC1 Homodimers and the Dimerization Domain

Figure 4:
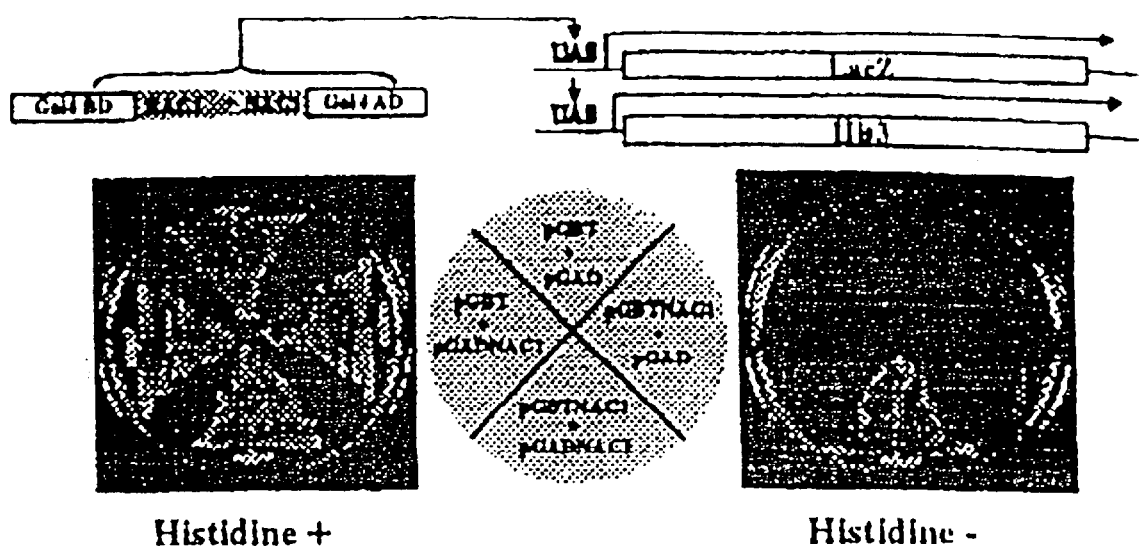
FIG. 4. Specific interaction between NAC1 and NAC1 in the yeast two-hybrid system assay. Yeast HF7c cells were co-transformed with plasmids expressing the GAL4$^{BD}$ alone or GAL4$^{BD}$-NAC1 fusion and the plasmids expressing the GAL4$^{AD}$ alone or fused to NAC1. (A) Cells were streaked on plates with or without histidine plus 10 mM 3-AT (Sigma) according to the distribution shown in the center of picture. The ability to grow in the absence of histidine depends on the functional reconstitution of a GAL4 activity. (B) The map of different deletions of NACl protein fusion to pGA vector. (C) The ability of interaction between the different deletions of NAC1 versions in two-hybrid system assay.
Figure 4:
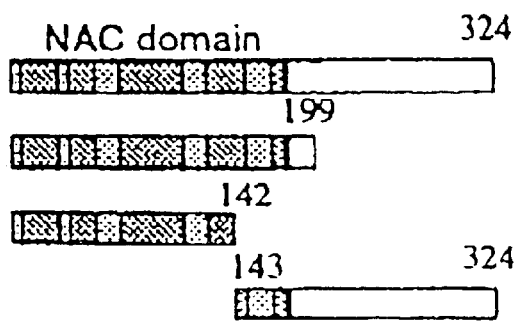

Transcription factors usually form dimers when they bind to DNA. To determine whether NAC1 forms dimers, we used a two-hybrid technique. The method was efficiently used to test dimerization and to study the protein-protein interaction including dimerization. The intact NAC1 was fused to both a Gal4 DNA activation domain and a DNA binding domain and cotransformed into reporter yeast. A clear interaction was observed when NAC1 was expressed by both vectors. Yeast were able to grow in three days even when 10 mM 3-AT was applied to block the nonspecific interactions (FIG. 4A). It must be mentioned that when NAC1 is expressed only in the DNA binding vector it can at a low level autoactivate the system so that the yeast can grow very slowly (FIG. 4A).

To identify the region of NAC1 required for dimerization, we constructed a series of deletions and analyzed their ability to form complexes in yeast. First a deletion of the C-terminus was made from amino acid 200 through the end of the protein. This left a protein of the first 199 amino acids. This 199 amino acid protein fragment contains the intact NAC domain and it was able to form dimers with intact NAC1. This 199 amino acid version gave no background signal like the wild-type full length version of NAC1. Therefore the 199 amino acid version was used as the fixed partner to test other deletions. A variety of different deletions in the activation domain vector were prepared (FIG. 4B). When the same deletion (lack of sequence beyond amino acid 199) was prepared in pGA the interaction was as strong as with the intact protein. But when the deletion affected block IV of the NAC domain and the construct contained only the first three intact blocks of the NAC domain, formation of dimers was abolished (FIG. 4C). Deletion of the N-terminus leaving only the latter half of block IV and intact block V resulted in a protein unable to form dimers. The data strongly support the conclusion that the NAM domain of NAC1 contains the dimerization domain. Block IV is important for dimer formation but block V itself is not enough to form a dimer. The NAC1 protein can form homodimers and this was confirmed by gel filtration. When bacteria expressed a protein of the first 199 amino acids of NAC1, the purified peptide including the complete NAC domain ran at twice the size in a native gel as in a denaturing gel.

Transactivation and the Transactivation Domain

Figure 5:
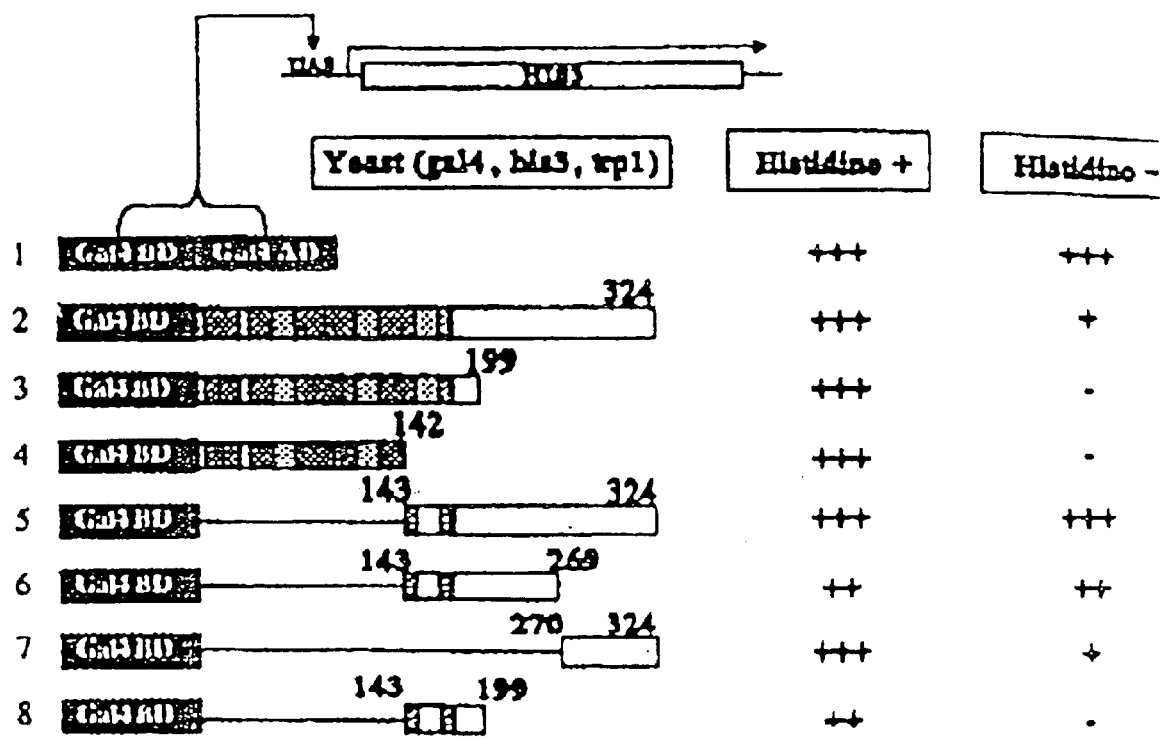
FIG. 5. Localization of transactivation domain in NAC1 protein. Different deletion version of NAC1 were cloned into Gal4 DNA binding vector and transformed into yeast strain is HF7c. Transformation mixture was plated on MM plates with histidine or without histidine supplement with necessary amino acids. The results were taken from three days growth plates.

In the yeast two-hybrid assay we found that NAC1 can auto-activate the system to a low level but the C-terminal deletion can not. Therefore we used a modified one-hybrid method with the hybrid transcription factor to identify the activation domain of the NAC1 gene. The vector pGBT8 which contains only the Gal4 DNA binding domain but no activation domain was used. Different deletions of the NAC1 gene were cloned into this plasmid in a fusion to the Gal4 DNA binding domain and the resulting plasmids were transformed into yeast containing $UAS_{gal1}$-CYC1-HIS3 reporter gene. Selection was performed on histidine minus plates. If the part of the fusion protein contained activation activity, Gal4 transcription should be reconstructed and switch on the promoter of HIS3. With histidine synthesis, yeast can grow on medium without histidine. The Gal4 activation domain was used as the positive control and it gave full activity as shown in FIG. 5. As mentioned above, the complete NAC1 protein gave only a low activation activity. The N-terminal fusion containing the first 132 amino acids or the first 199 amino acids gave no activity. Similarly, a fusion with a peptide fragment of amino acids 143–199 gave no activity. In contrast, a fusion containing amino acids 133 to the carboxy terminus fully activated the reporter gene giving a signal as strong as the positive control Gal 4 transcription factor. The use of a fusion containing only amino acids 143–269 also gave full activity. This is a highly acidic amino acid region. The C-terminal fusion containing only the last 54 amino acids resulted in low activity. The results indicate that the activation domain of NAC1 is located in the C-terminus Because the NAC family has been seen only in plants and not in other organisms, it was important to check the transactivation activity in plants. An in vivo experiment was devised to check the activation domain. Two plasmids were constructed. The first one carried the Gal4 DNA binding-MCS-Nos terminal cassette tagged with a CaMV 35S promoter. The tested gene can be cloned into MCS in frame with Gal4 DNA binding domain. The other plasmid contains the reporter gene construct 6xUAS-TATA-Luc which can express luciferase if some proteins can bind to the 6xUAS element to activate the promoter. Co-bombardment with the two plasmids together at different combinations demonstrated the system is reproducible and applicable. We used the activation domain from virus VP16 as a positive control and it gave a very high activity. In contrast, neither the second plasmid (pTALuc) alone nor it plus the vector pGal gave significant luciferase activity. A similar result was obtained as that from the yeast system. The full transactivation activity was identified in the peptide of amino acids 143–269. The last 54 amino acids also gave the low activity. The N-terminus of NAC1 gave no activity nor did the vector control itself. Both in yeast and in plant systems, it has been demonstrated that NAC1 contains a transactivation domain and the region corresponding to this activity is between amino acids 142–269.

Transgenic Arabidopsis Plants which Overexpress and Underexpress NAC1

In this study, a glucocorticoid-inducible transgenic system was used as previously described (Aoyama and Chua, 1997). A glucocorticoid-regulated transcription factor is encoded by a GVG whose transcription is controlled by the CaMV 35S promoter. The transcription of transgene is controlled by the glucocorticoid-activated promoter (6XUAS$_{gal4}$). The 1287 basepair complete NAC1 encoding cDNA (SEQ ID NO:1) was cloned into the binary plant transformation vector pTA7002 in both directions and separately transformed into Arabidopsis thaliana lansberg ecotype by a root transformation method. Overexpressing and underexpressing transgenic lines were selected from hygromycin containing medium. Six independent transgenic lines of overexpressing and 4 independent lines of underexpressing were selected. All of the lines segregated for one T-DNA locus according to hygromycin resistant segregation ratios.

Figure 6:
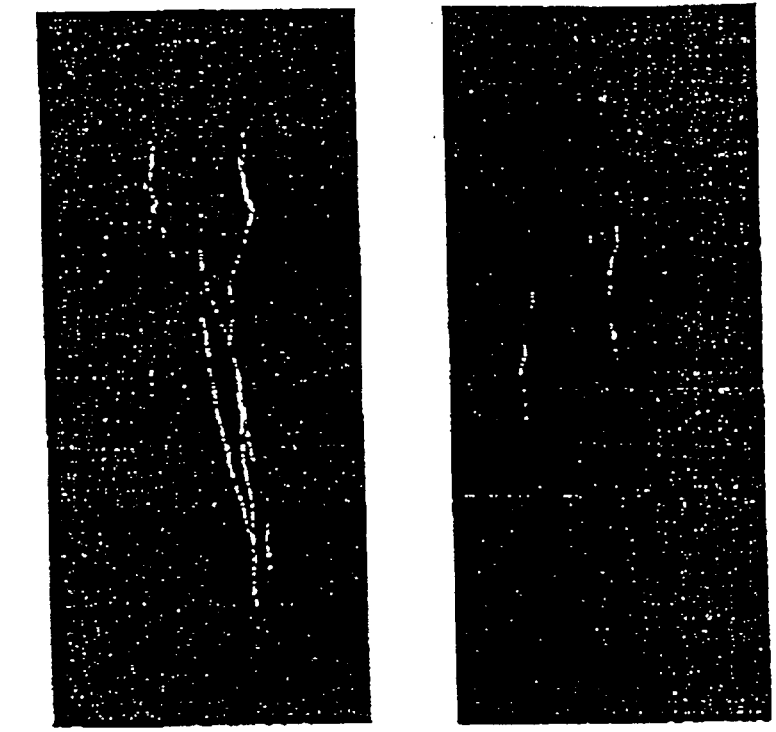
FIG. 6. Affect of overexpression of NAC1 in plants. (A) Wild-type plants grown in the absence of Dex. (B) Wild-type plants grown in the presence of Dex. (C) Transgenic plants grown in the absence of Dex. (D) Transgenic plants grown in the presence of Dex.
Figure 6:
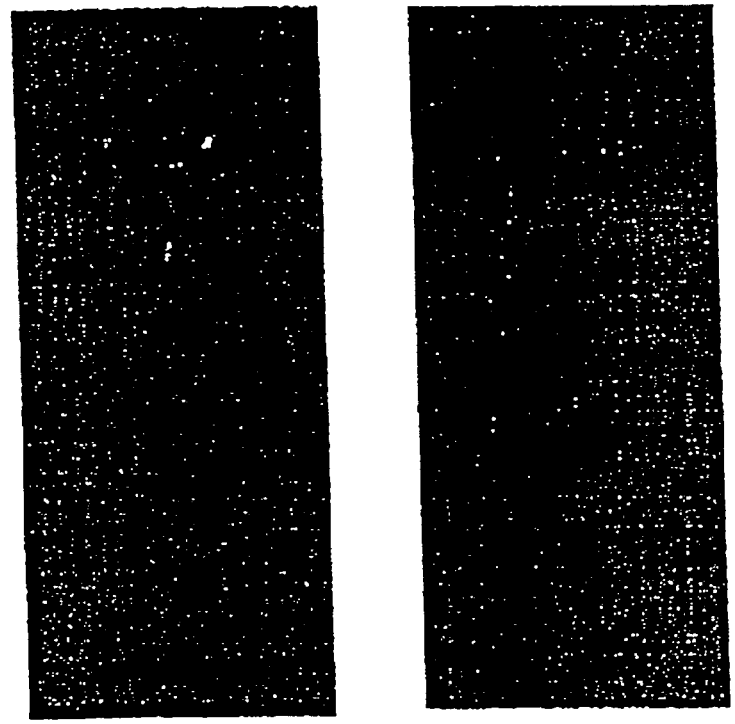

The six overexpressing transgenic plants were of three different phenotypes. Four of the lines were of one phenotype while the remaining two lines each showed a different phenotype. These latter two phenotypes are similar to antisense plants as will be described below. Studies of the first four lines of similar phenotype showed that those plants grow more quickly and grow larger than nontransgenic plants both under in vitro and in soil growth conditions. More lateral roots were produced when inducing conditions were employed, such as on plate vertical or in plantcon growths. Data is presented for in vitro growth conditions. Seedlings of different ages were transferred from MS medium to both MS medium and MS plus 10 iM Dexamethasone (Dex), then checked after one week of growth. Ten plants of each homozygous line were weighed after cleaning the agar or soil off of the plants. One week old seedlings transferred to Dex medium were 1.1 to 1.3 times heavier than uninduced plants, 15 day seedlings were 1.3 to 1.8 times heavier, and 25 day old seedlings were 1.4 to 2.6 times heavier. The increased weight in the induced plants resulted from bigger leaves, thicker stems and more roots, with the leaf size being the major contributor. Leaf epidermal cells from different parts of plants were analyzed by scanning electron microscopy (SEM). SEM showed that the cell size of old leaves was bigger than control cell size while there was no clear difference in cell size of new growth leaves. Vertical growth roots of a representative line are shown in FIG. 6. More and longer lateral roots were produced in Dex induced lines. Total RNA was prepared from 48 hour induced plants and mock controls and measured via Northern blots probed with the C-terminal specific probe for nac1. The results indicated that all four transgenic lines show that the transgene is expressed. The transgene mRNA size is larger than the native mRNA size and is easily distinguished.

The two remaining overexpression lines as well as all four selected lines of antisense transgenic plants showed some sharing of different combinations of phenotypes. One of the two overexpression lines and one of the antisense lines showed cotyledon curved-up phenotype in seedling stage. No clear phenotypes were detected in later vegetative inflorescence development stage. Two antisense lines showed very typical phenotypes in seedling stage as well as cuc2 mutant. In this case, single, heart-shaped and fused cotyledon and more severe, rosette seedlings were detected at a low percentage around 7–10% of germination seedlings. Most of these seedlings, which cannot produce the shoot apical meristem, died later.

One of the antisense lines and one overexpression line did not appear any different from uninduced plants during all seedling and vegetative growth stages. But at the stage of inflorescence development, floral organs were affected, particularly petals and stamens. The phenotypes were found in the first several flowers of the inflorescence. Those flowers have short petals and stamens, and in those with the more severe phenotypes the flower could not open at all. Some of them can open but clear short stamens can be seen. Those flowers were male and female-sterile. This kind of phenotype overlaps the overexpression of another Arabidopsis NAC family member—the NAP gene.

Transgenic Arabidonsis Plant Underexpression of C-terminal Specific NAC1 Gene

Figure 7:
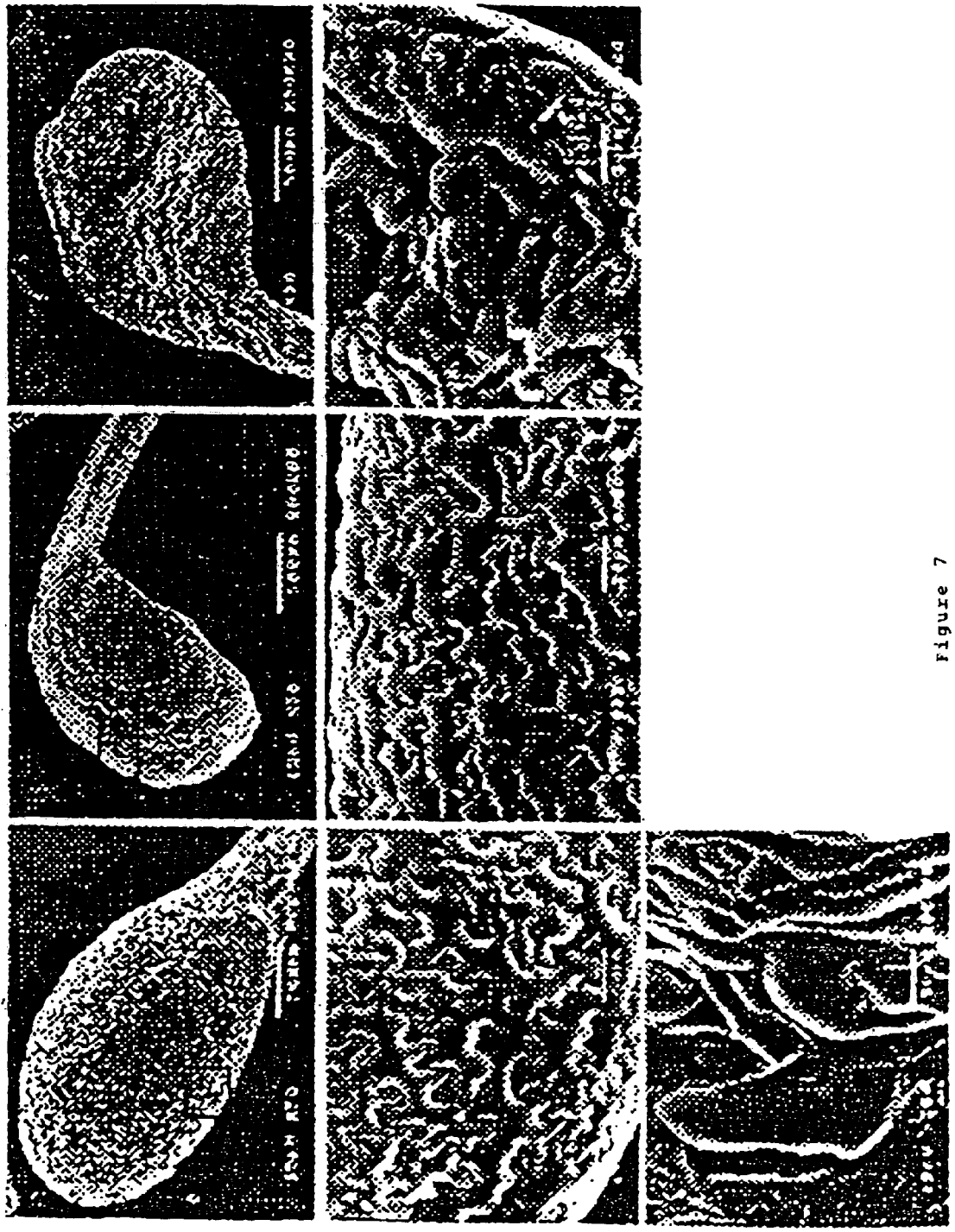
FIG. 7. Cotyledon developmental changes in C-terminal specific antisense plants. SEM shows abaxial surface of cotyledon. A and D (detail) are wild-type, B and E (detail) are no severe phenotype, C and F, G (detail) are severe phenotype. Boxes with letters in A, B and C show the regions that are detailed.

As members of the NAC gene family are highly conserved at the N-terminus, not only at the amino acid level but also at the nucleotide sequence level, antisense nucleic acids to this region will affect homologous genes as shown in petunia. Therefore, C-terminal specific antisense constructs were prepared using vector pTA7002 and transformed into Arabidopsis as described above. For this construct, we used the 0.6 kb BamHI-NotI C-terminal fragment. Northern blots developed only one band corresponding to the NAC1 gene in all tissues when using this fragment as probe for the four of 6 homozygous lines we selected for analysis. All showed similar phenotypes, mainly affected cotyledon and root development. No clear phenotypes were detected during all other stages of plant growth. One representative line of the C-specific antisense plants is described here. Cotyledons of wildtype or uninduced seedlings showed a slight curved-down and smooth surface. In the first week of germination no clear phenotype was detected in cotyledon development, but in 10 day old seedlings, 20 to 25% show severe cotyledon curved-up phenotype. A few also showed a curved-back phenotype. The phenomenon can be easily detected under light microscopy or even seen directly by eye. At the later stage, black dots can be seen on the surface of cotyledons. The abaxical epidermal cells were checked by SEM and abnormal cell expansion was found over all cotyledon surfaces, although different levels of severity were seen (FIG. 7). Those cells lost the normal puzzle-like structure and became disordered with different cell sizes and cell shapes (FIGS. 7C, 7F and 7G). Cotyledons of those to 80% seedlings which showed no severe or clear curved-up phenotype under light microscopy also were checked by SEM. SEM results indicated the surface cells of those cotyledons were also abnormal. Cells looked swollen and more expanded.

Figure 8:
FIG. 8. Wild-type or transgenic plant seeds with antisense NAC1 were germinated on MS or MS plus Dex medium. (A) Wild-type in the absence of Dex; (B) wild-type induced with Dex; (C) transgenic in the absence of Dex; and (D) transgenic induced with Dex.
Figure 8:
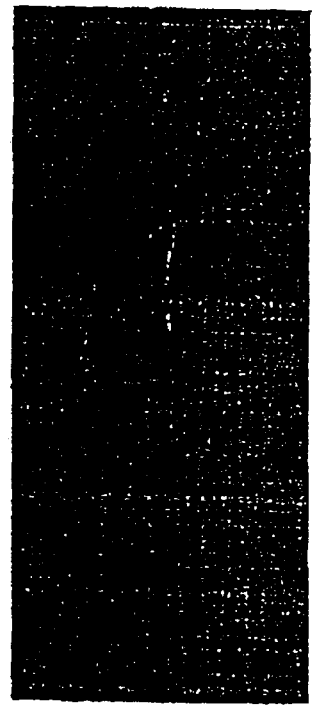
Figure 8:
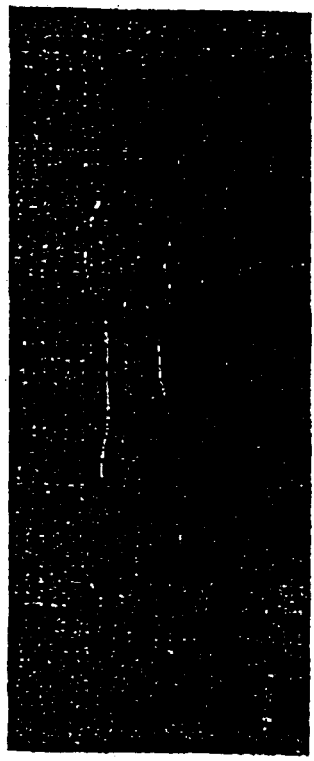
Figure 8:
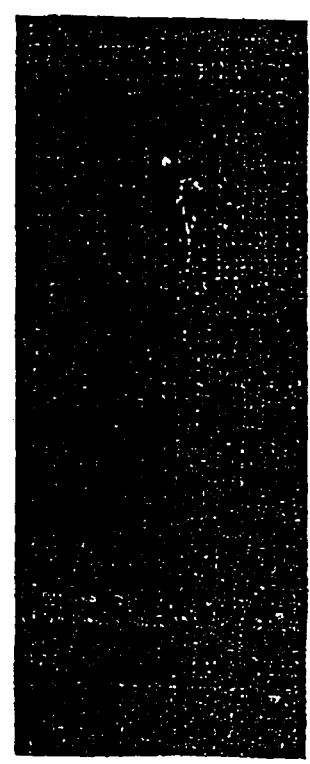

The root phenotypes were easily detected on vertical growth seedlings. Seeds were germinated on MS or MS plus Dex medium. After one week germination, seedlings were transferred to the same fresh medium and continuously grown for one week and then checked. A few roots were produced in seedlings which contained C-terminal antisense expression. Three lines had short or fewer lateral roots and one line almost had no lateral roots. Those seedlings which had short or fewer lateral roots were checked by microscope and it was found that the lateral roots can be initiated but cannot be elongated. Therefore the seedlings look as if they contain fewer roots in comparison to uninduced seedling (FIG. 8). Similar results were obtained from liquid growth C-terminal antisense plants. One week old seedlings were added to liquid MS or MS plus Dex medium and after 12 days growth uninduced roots are larger than induced roots of seedlings.

The present invention is further detailed in the following Examples, which are offered by way of illustration and are not intended to limit the invention in any manner. Standard techniques well known in the art or the techniques specifically described below are utilized.

EXAMPLE 1
Plant Materials and Growth Conditions

*Arabidopsis thaliana lansberg* ecotype was used for the experiments. Seeds were surface sterilized with 20% bleach plus 0.01% Triton X-100 and washed three times with sterile water. After the final wash, 0.15% agarose was added to the seed and they were plated on MS or MS plus Dexamethasone (Dex) at different concentrations with 3% sucrose. Plates were incubated at 4° C. for two days and transferred to a tissue culture room at 22° C. under long day (16 hour light/8 hour dark) conditions. After two to three weeks, seedlings were potted in soil and grown in a growth chamber with a photoperiod of 16 hours light/8 hours dark at 22° C. and 75% humidity.

For Dex treatment, dexamethasone (Sigma) was dissolved in DMSO to make 100 mM dexamethasone stock solution which was stored at −20° C. For in vitro growth plants, Dex was added to the plates at 0.1, 1 and 10 iM. Dex was continually added to medium once a week. Photocon and plantcon were used. Dex was first dissolved in sterile water at 1/25th volume of medium and then was added to the surface of the medium. For treatment of soil growth plants, Dex was added to sterile water containing 0.01% Triton X-100 at 30 iM then sprayed to cover all surfaces of the plant, once every two days. For mock controls, sterile water containing 0.01% Triton X-100 was sprayed on the same number of plants.

EXAMPLE 2
Transformation Constructs and Plant Transformation

The binary transformation plasmid pTA7002 containing the complete two-component glucocorticoid-inducible system (Aoyama and Chua, 1997) was used as a vector. For overexpression and complete antisense constructs, a 1287 basepair SalI-NotI fragment containing the complete NAC1 encoding cDNA was blunt-ended and cloned into XhoI digested and calf intestinal alkaline phosphatase treated pTA7002 vector. To prepare a C-terminal specific antisense construct, the 605 basepair BamHI-NotI fragment containing C-terminal specificregion of NAC1 encoding cDNA was blunt ended and cloned into pTA7002 vector as mentioned above. For transgenic constructs containing GFP-NAC1 fusion cassette, an NaeI-SalI fragment generated by PCR containing just NAC1 coding region was cloned into an intermediate GFP fusion vector pGFP2(GA)5II digested by NaeI and SalI to produce plasmid pGFPNAC1. Then the GFPNAC1 fusion was cut out by XbaI plus PacI and cloned into pTA7002 vector by using the same procedures as above. *Arabidopsis thaliana lansberg* roots were used as the plant material for transformation (Valvekens et al., 1988). T2 seeds were germinated on SM plates containing 20 ig/mL hygromycin B to select resistant plants and transferred to soil to generate and to obtain homozygous T3 seeds. Two independent lines of homozygous T4 plants with a single insertion from each construct were used for detail analysis.

EXAMPLE 3
Northern Analysis and Whole Mount In Situ Analysis

Total RNA was isolated from different tissues by using the Qiagen RNA preparation kit. Northern blot analysis was performed according to Nagy et al. (1988). For probes, a PCR fragment covered amino acids 200 to 324 was labeled with á-$^{32}$P dCTP using a Redi-primed labeling kit (Amersham International). Whole plants or flowers were fixed for whole-mount in situ hybridizations. Antisense RNA from the C-terminal specific region of NAC1 was labeled with digoxigenin UTP (Boehringer Biochemica, Mannheim, Germany). The hybridization was detected with anti-digoxigenin Fab fragment conjugated to alkaline phosphatase. As control probes, sense transcripts were prepared from the same clone using T3 transcriptase.

EXAMPLE 4
Yeast Two-Hybrid Analysis

Two-hybrid analysis (Bartel et al., 1993; Fields and Song, 1989; Chevray and Nathans, 1992; Lee et al., 1995) was applied to dimerization analysis. The yeast strain HF7c (MATa ura3–52 his3–200 ade2–101 lys2–801 trp1–901 leu2–3,112 gal4–542 gal 80–538 LYS2::GAL1$_{UAS}$-GAL1$_{TATA}$-HIS3 URA3::GAL4$_{17mers(x3)}$-CyC1$_{TATA}$-LacZ which contains the two reporter genes LacZ and HIS3 was used. Yeast cotransformation with plasmids carrying the different Gal4 DNA binding domain and the Gal4 activation domain fusion was performed by methods known to those of skill in the art. See, e.g., Burke and Olson, 1986; Rudolph et al., 1985; Sakai et al., 1984. Other conditions have been described in detail elsewhere and are well known to those of skill in the art. To corroborate the interaction between the two fusion proteins, â-galactosidase activity was assayed by a replica filter assay.

Two versions of NAC1 were cloned into the Gal4 DNA binding domain vector pGBT8, a derivative of pGBT9 (Clontech) which contains a more versatile polylinker. Plasmid pGBNACl1–324 contains the complete open reading frame for NAC1 fused to the Gal4 DNA binding domain. Plasmid pGBNACl1–199 contains only the nucleic acid encoding the first 199 amino acids on the same vector. Different truncated versions of NAC1 were fused to the Gal4 activation domain vector pGAD424. Plasmid pGANAC1 1–324 contains the complete open reading frame for NAC1. Plasmid pGANAC1 1–199 contains nucleic acid encoding the first 199 amino acids of NAC1. Plasmid pGANAC1 1–142 contains nucleic acid encoding the first 142 amino acids of NAC1 and plasmid pGANAC1 143–324 contains nucleic acid encoding amino acids from 143 to the C-terminus of the peptide.

EXAMPLE 5
Transfection of Epidermal Cells by Particle Bombardment

Petals were cut into 2×2 cm pieces and put on a filter soaked with liquid MS medium. 2 ig of each plasmid combination was used for each shoot in a vacuum of 27 inches of mercury using a helium pressure of 1100 psi. After bombardment plates were incubated in plant growth room overnight (16 hours) and 50 mM luciferin (Promega) was sprayed on the material. The results were checked after 10 minutes incubation.

EXAMPLE 6
Production of GST-Fusion Proteins and DNA Binding

PCR product containing the complete coding region of NAC1 gene was cloned into pGEX-4-2T to produce PGST-NAC1 fusion construct. GST-NAC1 1–199 was generated by digesting pGST-NAC1 with BamHI and SalI and treated with Klenow and religated to produce pGST-NAC1 1–199 which contains only the first 199 amino acids of NAC1 protein. GST-NAC1 1–132 was obtained by cutting pGST-NAC1 with XhoI plus SalI and religated. GST-NAC1 133–324 was constructed by cloning an XhoI-NotI fragment from the original cDNA clone into pGEX-4-2T. Plasmids were transformed into E. coli BL21(DE3). Transformants were grown to an $OD_{600}$ of 0.6 to 0.9 and then induced to express the fusion protein at 30° C. for 4 hours by the addition of IPTG to 0.4 mM. Cells were washed once with PBS and resuspended in GST buffer (GCB: 50 mM Tris-HCl at pH 8.0, 200 mM NaCl, 1 mM EDTA, 1% Triton X-100, 10 mM â-mercaptoethanol, 5 ig/mL each of leupeptin, pepstatin and aprotinin, and 1 mM PMSF). Cells were lysed by sonication on ice (5×30 seconds), and the lysates were cleared by centrifugation (15 minutes at 12,000 rpm). The fusion protein was recovered by affinity chromatography on glutathione-Sepharose beads (Pharmacia). The DNA binding reaction contained $2 \times 10^5$ cpm DNA probe, 5 iL of 4×reaction buffer (100 mM NaCl, 40 mM HEPES, pH 7.5, 2 mM EDTA, 20% glycerol, 140 mM â-mercaptoethanol), 0.5 ig poly dIdC (Pharmacia), 1 iL 1% Nonidet P40 and different amount of proteins in a total volume of 20 iL. 10 iL of reaction were used on a 4–6% 1/2 TBE native gel. A 100 basepair BamHI fragment containing 35S −90 region was labeled by $a$-$^{32}$PdCTP in a Klenow labeling reaction. details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Aida M, et al. (1997). The Plant Cell 9:841–857.
Aoyama T and Chua N-H. (1997). Plant J. 11:605–612.
Bartel P L, et al. (1993). "Using the 2-hybrid system to detect protein-protein interactions." In Cellular Interactions in Development: A Practical Approach, Oxford University Press, pp. 153–179.
Burke D T and Olson M V (1986). DNA 5:325–332.
Chevray P M and Nathans D N (1992). Proc. Natl. Acad. Sci. USA 89:5789–5793.
Fields S and Song O-K (1989). Nature 340:245–246.
John I, et al. (1997). Plant Mol. Biol. 33:641–651.
Lee J E, et al. (1995). Science 268:836–844.
Nagy F, et al. (1988). In Plant Molecular biology Manual, B4 (Gelvin S and Schilperoort R, eds). Dordrecht, The Netherlands; Kluwer Academic Publishers, pp.1–12.
Rudolph H, et al. (1985). Gene 36:87–95.
Sablowski R W M and Meyerowitz E M (1998). Cell 92:93–103.
Sakai K, et al. (1984). Mol. Cell. Biol. 4:651–656.
Souer E, et al. (1996). Cell 85:159–170.
Valvekens D, et al. (1988). Proc. Natl. Acad. Sci. USA 85:5536–5540.
Xia Q, et al. (1996). Plant J. 10:761–769.

What is claimed is:

1. An isolated nucleic acid comprising nucleotides 89–1060 of SEQ ID NO.:1.

2. An isolated nucleic acid encoding the protein of SEQ ID NO:2.

3. A transformed plant comprising the nucleic acid of claim 2.

4. A transformed plant cell comprising the nucleic acid of claim 2.

5. A method of increasing the growth of a plant comprising overexpressing a nucleic acid encoding the protein of SEQ ID NO.: 2 in said plant as compared to a non-transformed plant, wherein said overexpression causes the increased growth of the plant.

6. The method of claim 5 wherein said plant produces larger leaves than a plant not overexpressing said protein.

7. The method of claim 5 wherein said plant produces larger roots than a plant not overexpressing said protein.

8. The method of claim 5 wherein said plant produces more lateral roots than a plant not overexpressing said protein.

* * * * *

SEQUENCE LISTING

```
<160> NUMBER OF SEQ ID NOS: 2

<210> SEQ ID NO 1
<211> LENGTH: 1287
<212> TYPE: DNA
<213> ORGANISM: Arabidopsis thaliana
<220> FEATURE:
<221> NAME/KEY: CDS
<222> LOCATION: (89)..(1060)

<400> SEQUENCE: 1
gtcgaccacg cctccgtctt tatctctctt ttcctcttaa ccatccacta atcaaacact      60
aaaacctaga aaaaaaagg atcaaatc atg gag acg gaa gaa gag atg aag          112
                              Met Glu Thr Glu Glu Glu Met Lys
                                1               5 gaa agt agt ata agc atg gtg gag gca aag ttg cct ccg gga ttc aga       160
Glu Ser Ser Ile Ser Met Val Glu Ala Lys Leu Pro Pro Gly Phe Arg
       10                  15                  20 ttt cac ccg aag gac gat gag ctt gtc tgc gat tac ttg atg aga cga       208
Phe His Pro Lys Asp Asp Glu Leu Val Cys Asp Tyr Leu Met Arg Arg
 25                  30                  35                  40 tcg ctt cac aat aat cat cga cca cct ctt gtc ctg atc caa gtc gat       256
Ser Leu His Asn Asn His Arg Pro Pro Leu Val Leu Ile Gln Val Asp
                     45                  50                  55 ctc aac aag tgt gag cct tgg gac atc cca aaa atg gca tgc gtg gga       304
Leu Asn Lys Cys Glu Pro Trp Asp Ile Pro Lys Met Ala Cys Val Gly
                 60                  65                  70
```

```
ggg aag gat tgg tat ttc tac agc caa aga gac cga aaa tac gcg acg      352
Gly Lys Asp Trp Tyr Phe Tyr Ser Gln Arg Asp Arg Lys Tyr Ala Thr
         75                  80                  85 ggg ctg aga act aac cga gca acg gcc acc gga tat tgg aaa gcc acc      400
Gly Leu Arg Thr Asn Arg Ala Thr Ala Thr Gly Tyr Trp Lys Ala Thr
 90                  95                 100 ggc aaa gac aga acc att cta aga aag ggt aag cta gtt ggg atg agg      448
Gly Lys Asp Arg Thr Ile Leu Arg Lys Gly Lys Leu Val Gly Met Arg
105                 110                 115                 120 aag aca ttg gtt ttc tat caa ggt cga gct cct cga ggc cgt aaa acc      496
Lys Thr Leu Val Phe Tyr Gln Gly Arg Ala Pro Arg Gly Arg Lys Thr
                125                 130                 135 gat tgg gtc atg cac gaa ttc cgt ctc caa gga tct cat cat cct ccc      544
Asp Trp Val Met His Glu Phe Arg Leu Gln Gly Ser His His Pro Pro
                140                 145                 150 aat cat tct ctg agc tct cca aag gaa gac tgg gtc ttg tgt agg gta      592
Asn His Ser Leu Ser Ser Pro Lys Glu Asp Trp Val Leu Cys Arg Val
                155                 160                 165 ttc cat aag aat acg gaa gga gtt ata tgt aga gac aac atg gga agc      640
Phe His Lys Asn Thr Glu Gly Val Ile Cys Arg Asp Asn Met Gly Ser
170                 175                 180 tgt ttt gat gag aca gcc tct gca tcg ctt cct cca ctg atg gat cct      688
Cys Phe Asp Glu Thr Ala Ser Ala Ser Leu Pro Pro Leu Met Asp Pro
185                 190                 195                 200 tac atc aac ttt gac caa gaa ccc tct tct tat ctc agt gat gat cat      736
Tyr Ile Asn Phe Asp Gln Glu Pro Ser Ser Tyr Leu Ser Asp Asp His
                205                 210                 215 cac tac atc atc aat gag cac gta ccc tgc ttc tcc aat ttg tca cag      784
His Tyr Ile Ile Asn Glu His Val Pro Cys Phe Ser Asn Leu Ser Gln
                220                 225                 230 aac caa acc tta aac tcg aac cta acc aac tca gtc tct gaa ctc aag      832
Asn Gln Thr Leu Asn Ser Asn Leu Thr Asn Ser Val Ser Glu Leu Lys
                235                 240                 245 att cca tgc aag aac cct aac ccc ttg ttt act ggt ggt tca gcc tca      880
Ile Pro Cys Lys Asn Pro Asn Pro Leu Phe Thr Gly Gly Ser Ala Ser
250                 255                 260 gcc acg ctc aca ggc ctc gac tca ttc tgt tct tca gat cag atg gtt      928
Ala Thr Leu Thr Gly Leu Asp Ser Phe Cys Ser Ser Asp Gln Met Val
265                 270                 275                 280 ctc aga gct cta ctc agt cag ctc act aag att gat gga agc ctc ggg      976
Leu Arg Ala Leu Leu Ser Gln Leu Thr Lys Ile Asp Gly Ser Leu Gly
                285                 290                 295 cct aaa gaa tca cag agt tat gga gaa ggt agc tcg gag agc ctc ctg     1024
Pro Lys Glu Ser Gln Ser Tyr Gly Glu Gly Ser Ser Glu Ser Leu Leu
                300                 305                 310 acc gac atc ggt att cca agc act gtt tgg aat tgc tgatgatcga          1070
Thr Asp Ile Gly Ile Pro Ser Thr Val Trp Asn Cys
                315                 320 gtgtaacgag agttactatt gctatattcc tatccatgat tggaacaatt cttcgggggg   1130
aaataacgtg tgcttgtctg attgtacaaa catttcctca ctcttgtacc cacggtagat   1190
tcatgtaaaa taccacttat gacgctagac atacatatat ttcatcgtag ttccatttgt   1250
ttcaaaaaaa aaaaaaaaaa aaaaaaaggg cggccgc                            1287

<210> SEQ ID NO 2
<211> LENGTH: 324
<212> TYPE: PRT
<213> ORGANISM: Arabidopsis thaliana
```

-continued

```
<400> SEQUENCE: 2

Met Glu Thr Glu Glu Met Lys Glu Ser Ser Ile Ser Met Val Glu
 1               5                  10                  15

Ala Lys Leu Pro Pro Gly Phe Arg Phe His Pro Lys Asp Asp Glu Leu
             20                  25                  30

Val Cys Asp Tyr Leu Met Arg Arg Ser Leu His Asn Asn His Arg Pro
         35                  40                  45

Pro Leu Val Leu Ile Gln Val Asp Leu Asn Lys Cys Glu Pro Trp Asp
     50                  55                  60

Ile Pro Lys Met Ala Cys Val Gly Gly Lys Asp Trp Tyr Phe Tyr Ser
 65                  70                  75                  80

Gln Arg Asp Arg Lys Tyr Ala Thr Gly Leu Arg Thr Asn Arg Ala Thr
                 85                  90                  95

Ala Thr Gly Tyr Trp Lys Ala Thr Gly Lys Asp Arg Thr Ile Leu Arg
            100                 105                 110

Lys Gly Lys Leu Val Gly Met Arg Lys Thr Leu Val Phe Tyr Gln Gly
        115                 120                 125

Arg Ala Pro Arg Gly Arg Lys Thr Asp Trp Val Met His Glu Phe Arg
    130                 135                 140

Leu Gln Gly Ser His His Pro Pro Asn His Ser Leu Ser Ser Pro Lys
145                 150                 155                 160

Glu Asp Trp Val Leu Cys Arg Val Phe His Lys Asn Thr Glu Gly Val
                165                 170                 175

Ile Cys Arg Asp Asn Met Gly Ser Cys Phe Asp Glu Thr Ala Ser Ala
            180                 185                 190

Ser Leu Pro Pro Leu Met Asp Pro Tyr Ile Asn Phe Asp Gln Glu Pro
        195                 200                 205

Ser Ser Tyr Leu Ser Asp Asp His His Tyr Ile Ile Asn Glu His Val
    210                 215                 220

Pro Cys Phe Ser Asn Leu Ser Gln Asn Gln Thr Leu Asn Ser Asn Leu
225                 230                 235                 240

Thr Asn Ser Val Ser Glu Leu Lys Ile Pro Cys Lys Asn Pro Asn Pro
                245                 250                 255

Leu Phe Thr Gly Gly Ser Ala Ser Ala Thr Leu Thr Gly Leu Asp Ser
            260                 265                 270

Phe Cys Ser Ser Asp Gln Met Val Leu Arg Ala Leu Leu Ser Gln Leu
        275                 280                 285

Thr Lys Ile Asp Gly Ser Leu Gly Pro Lys Glu Ser Gln Ser Tyr Gly
    290                 295                 300

Glu Gly Ser Ser Glu Ser Leu Leu Thr Asp Ile Gly Ile Pro Ser Thr
305                 310                 315                 320

Val Trp Asn Cys
```